United States Patent [19]

Eckhardt et al.

[11] Patent Number: 4,518,785
[45] Date of Patent: May 21, 1985

[54] MALONDIALDEHYDE TETRAALKYLACETALS AND THEIR PREPARATION

[75] Inventors: Heinz Eckhardt, Frankenthal; Klaus Halbritter, Mannheim; Wolfgang Rohr, Wachenheim, all of Fed. Rep. of Germany

[73] Assignee: BASF Aktiengesellschaft, Ludwigshafen, Fed. Rep. of Germany

[21] Appl. No.: 437,683

[22] Filed: Oct. 29, 1982

[30] Foreign Application Priority Data

Nov. 19, 1981 [DE] Fed. Rep. of Germany ....... 3145709

[51] Int. Cl.$^3$ .................. C07D 317/00; C07D 317/22
[52] U.S. Cl. .................................... 549/453; 568/594; 568/603
[58] Field of Search ................. 549/453; 568/594, 603

[56] References Cited
FOREIGN PATENT DOCUMENTS 493635  6/1953  Canada ................................ 568/603

0058928  1/1982  European Pat. Off. ........... 568/603

OTHER PUBLICATIONS

Chemical Abstracts 89:180072w, (1981), 10th Collective, p. 18922cs.
Houben-Weyl, Methoden der Organischen Chemie vol. 6/3, pp. 248 and 311, (1964).
Chemical Abstracts 68:2828d, (1968).
Chemical Abstracts 83:163568u, (1975).
Mendoza et al., J. Organmet. Chem., 1978, pp. 149–157.

*Primary Examiner*—Ethel G. Love
*Attorney, Agent, or Firm*—John H. Shurtleff

[57] ABSTRACT

Novel malondialdehyde tetraalkylacetals and the preparation of malondialdehyde tetraalkylacetals by reacting alkyl formates, oxiranes and alkyl vinyl ethers in the presence of a halide of boron, antimony(V), iron(III), tin(II or IV) and/or zinc.

The malondialdehyde tetraalkylacetals obtainable by the process of the invention are valuable starting materials for the preparation of dyes, pest control agents and pharmaceuticals.

17 Claims, No Drawings

MALONDIALDEHYDE TETRAALKYLACETALS AND THEIR PREPARATION

The invention relates to novel malondialdehyde tetraalkylacetals and to the preparation of malondialdehyde tetraalkylacetals by reacting alkylformates, oxiranes and alkyl vinyl ethers in the presence of a halide of boron, antimony(V), iron(III), tin(II or IV) and/or zinc.

Houben-Weyl, Methoden der Organischen Chemie, Volume 6/3, page 248 discloses the reaction of vinyl ethers with orthoformic acid esters in the presence of an acid catalyst to give malondialdehyde tetraalkylacetals.

We have found that malondialdehyde tetraalkylacetals of the formula $$\begin{array}{c} R^1-O \\ \phantom{R^1-}\diagdown \\ \phantom{R^1-O}CH-CH_2-CH \\ \phantom{R^1-}\diagup \\ R^1-O \end{array} \begin{array}{c} O-R^1 \\ \diagup \\ \\ \diagdown \\ O-R^1 \end{array} \qquad I$$

where the individual radicals $R^1$ may be identical or different and each is alkyl, or alkoxy-substituted alkyl, and 2 adjacent $R^1$'s may also be $$-CH_2-CH-,$$
$$\phantom{-CH_2-}|$$
$$\phantom{-CH_2-}R^2$$

where $R^2$ is hydrogen or alkyl, are obtained in an advantageous manner by catalytic reaction of vinyl ethers with formic acid derivatives, when an alkyl formate of the formula $$HCOOR^1 \qquad II$$

is reacted with an oxirane of the formula $$\begin{array}{c} O \\ \diagup \phantom{..} \diagdown \\ H_2C\phantom{....}CH-R^2 \end{array} \qquad III$$

and an alkyl vinyl ether of the formula $$CH_2=CH-OR^1 \qquad IV$$

where $R^1$ and $R^2$ have the above meanings, in the presence of a halide or boron, antimony(V), iron(III), tin(II or IV) and/or zinc.

We have also found the novel 2-(2′,2′-dialkoxyethyl)-4-alkyl-(1,3)-dioxolanes of the formula $$\begin{array}{c} H_2C-O \\ \phantom{H_2}| \phantom{-}\diagdown \\ \phantom{HC}\phantom{-}CH-CH_2-CH \\ \phantom{H_2}| \phantom{-}\diagup \\ HC-O \\ \phantom{H}| \\ R^2 \end{array} \begin{array}{c} OR^1 \\ \diagup \\ \\ \diagdown \\ OR^1 \end{array} \qquad Ia$$

where the individual radicals $R^1$ may be identical or different and each is alkyl or alkoxy-substituted alkyl, and the pair of $R^1$ radicals may also be $$-CH_2-CH-,$$
$$\phantom{-CH_2-}|$$
$$\phantom{-CH_2-}R^2$$

if $R^2$ is hydrogen or alkyl of more than one carbon atom.

Where methyl formate, 2-methyloxirane and methyl vinyl ether are used, the reaction may be represented by the following equation:

$$2HCOCH_3 + 2CH_2\text{—}CH\text{—}CH_3 + 2CH_3O\text{—}CH=CH_2 \longrightarrow$$

[reaction scheme showing intermediate dioxolane acetal products and final tetramethyl acetal]

Compared to the conventional process, the process according to the invention gives malondialdehyde tetraalkylacetals more simply and more economically, in high yield and good purity.

A further advantage of the novel process is that use and handling of the hydrolysis-sensitive orthoformates, whose preparation entails the unavoidable production of a large amount of salt and the handling of very toxic starting materials, and necessitates corrosion-resistant apparatus, is avoided. The preparation, according to the invention, of malondialdehyde tetraalkylacetals I from simple alkylformates is free from all the disadvantages of preparing and using the orthorformates.

It was not to be expected from the prior art that alkyl vinyl ethers would undergo direct adduct formation with alkylformates to give malondialdehyde derivatives. All the above advantages are surprising in the light of the prior art.

The starting materials II, III and IV may be reacted in stoichiometric amounts or using an excess of any component relative to the others. Preferably, from 0.5 to 3.0, advantageously from 1.0 to 2.0, moles of starting material III and from 0.5 to 3.0, advantageously from 1.0 to 2.0, moles of starting material II are reacted per mole of starting material IV. Preferred starting materials II, III and IV and accordingly preferred end products I are those where the individual radicals $R^1$ are identical or different and each is alkyl of 1 to 6 carbon atoms which is unsubstituted or substituted by alkoxy of 1 to 4 carbon atoms, or two adjacent $R^1$'s, may be $$-CH_2-CH-,$$
$$\phantom{-CH_2-}|$$
$$\phantom{-CH_2-}R^2$$

where $R^2$ is hydrogen or alkyl of 1 to 6 carbon atoms. The above radicals may in addition be substituted by groups which are inert under the reaction conditions, for example alkyl or alkoxy, each of 1 to 4 carbon atoms.

For example, the following alkylformates II may be used: methyl, ethyl, propyl, isopropyl, butyl, isobutyl, sec.-butyl, tert.-butyl, pentyl or hexylformate, and corresponding formates where alkyl is substituted by methoxy, ethoxy, propoxy, isopropoxy, butoxy, isobutoxy, sec.-butoxy or tert.-butoxy.

Examples of suitable starting materials III are oxirane and 2-methyl-, 2-ethyl-, 2-propyl-, 2-isopropyl-, 2-butyl-, 2-isobutyl-, 2-sec.-butyl-, 2-tert.-butyl-, 2-pentyl- and 2-hexyl-oxirane.

Examples of suitable starting materials IV are methyl, ethyl, propyl, isopropyl, butyl, isobutyl, sec.-butyl and tert.-butyl vinyl ether and corresponding alkyl vinyl ethers where alkyl is substituted by methoxy, ethoxy, propoxy, isopropoxy, butoxy, isobutoxy, sec.-butoxy or tert.-butoxy.

The halides used as catalysts are advantageously employed in an amount of from 0.05 to 5.0, especially from 0.1 to 1.0, % by weight, based on the amount by weight of starting material II. Adducts of the halide, for example $BF_3$—$HCOOCH_3$ and $BF_3$—$C_2H_5OC_2H_5$, may also be used.

$BF_3$ and its adducts are preferred. In preferred embodiments, boron halides and antimony halides are added simultaneously with, but separately from, the alkylformate, whilst the other halides mentioned above are added simultaneously with, but separately from, the alkyl vinyl ether, to the reaction mixture. Amongst the halides, fluorides and chlorides are preferred. Conventional organic or inorganic bases (for example metal oxides, carbonates, hydroxides or alcoholates, and amines and amides) may be used to neutralize the catalyst which is completely or partially dissolved in the reaction mixture.

The reaction is as a rule carried out at from −80° to +200° C., preferably from 0° to 100° C., advantageously from 0° to 70° C., especially from 20° to 70° C., under atmospheric, reduced or superatmospheric pressure, advantageously under from 1 to 4 bar, continuously or batchwise. Preferably, it is carried out in a temperature range between 0° C. and the boiling point of the reaction mixture. Examples of suitable solvents are aromatic and aliphatic hydrocarbons, halohydrocarbons, carboxylic acid esters and ethers. Preferably, the reaction is carried out in excess alkylformate; if the latter is used as a solvent, preferably from 5 to 40, advantageously from 10 to 20, moles of starting material II are used per mole of starting material IV.

The reaction may be carried out as follows: a mixture of catalyst, starting materials II, III and IV and organic solvent, if any, is kept at the reaction temperature for from 1 to 15 hours. In batchwise operation, the catalyst is advantageously mixed with the alkylformate and the solvent, if any, and the oxirane, or a solution of the oxirane in a solvent, which may also contain alkylformate, is added continuously to the reaction mixture. The time required for this may advantageously be from 10 to 600 minutes, preferably from 15 to 150 minutes. Thereafter, the solvent and excess alkylformate can advantageously be removed by distillation until the boiling point of the reaction mixture is, preferably, from 50° to 80° C.; this distillation is not essential to the process but is advantageous, since it makes it possible to avoid purifying the recovered alkylformate and the solvent. An alkyl vinyl ether, with or without a solvent, is then added to the reaction mixture obtained above, over 1–5 hours, preferably 1–2 hours. After completion of the reaction, the catalyst is advantageously neutralized with the above bases and the end product isolated in a conventional manner, for example by distillation. On distillation, the first runnings obtained contain some end products and are advantageously added to a subsequent reaction mixture batch, prior to adding the alkyl vinyl ether. This makes it possible to increase the yield.

A preferred embodiment of the continuous process advantageously employs a cascade of three reactors. Into the first, a solution of an oxirane in an alkylformate, with or without an additional solvent, and a solution of $BF_3$ in a solvent are introduced. The reaction mixture which leaves the reactor after a predetermined residence time, which can advantageously be from 10 to 200 minutes, preferably from 10 to 30 minutes, is freed from excess alkylformate and solvent in a distillation apparatus. This distillate is recycled to the first reactor, whilst the distillation residue flows into the second reactor, where it is mixed with an alkyl vinyl ether. After a predetermined residence time, which can again advantageously be from 10 to 200 minutes, preferably from 30 to 60 minutes, the reaction mixture is treated, in the third reactor, with one of the above bases, preferably a liquid base, to neutralize the catalyst. The end product is isolated by conventional methods, for example distillation. The first runnings from the distillation, which again contain end product, are advantageously recycled to the second reactor to increase the yield. In this procedure, again, it is possible to dispense with the above distillation of the reaction mixture from the first reactor, and only to separate off the excess alkylformate and solvent in the final distillation; this material can then, where necessary after purification, be recycled to the first reactor.

The end products I obtained are in general mixtures containing a main product, for example 2-(2′,2′-dimethoxyethyl)-4-methyl-(1,3)-dioxolane, and by-products which are however also largely end products I, for example 1,1,3,3-tetramethoxypropane, malondialdehyde bis-1,2-propylene-acetal, 1-methoxypropoxy-1,3,3-trimethoxypropane, 2-(2-methoxy-2-methoxypropoxyethyl)-4-methyl-(1,3)-dioxolane.

The malondialdehyde tetraalkylacetals obtainable by the process of the invention are valuable starting materials for the preparation of dyes, pest control agents and pharmaceuticals. They may be used as intermediates for the synthesis of heterocyclic compounds (for example pyrazole, isoxazole, pyrimidine, 2-aminopyrimidine and pyrimidone), which in turn are used as intermediates for crop protection agents, dyes and active compounds for pharmaceuticals.

In the examples, parts are by weight and bear the same relation to parts by volume as that of the kilogram to the liter.

EXAMPLE 1

1,000 parts of methylformate and one part of $BF_3$—$HCOOCH_3$ are introduced into a reactor and the mixture is heated to 30° C. A mixture of 100 parts of 1,2-propylene oxide and 100 parts of methylformate is then added over 3.5 hours at 30°–32° C. After a further 15 minutes, one part of $BF_3.HCOOCH_3$ is added to the reaction mixture, and a mixture of 81 parts of methyl vinyl ether and 50 parts of methylformate is then added over 2 hours at 25°–32° C. The catalyst is then neutralized with 5 parts of $NaOCH_3$ and the reaction mixture subjected to fractional distillation. At 55°–85° C./1 mbar, 171 parts of end product containing 83% of compound I are obtained, representing a yield of 48% of theory, based on propylene oxide, of 59% of theory, based on methyl vinyl ether.

The end product I has the following composition: 1,1,3,3-tetramethoxypropane (8%) of boiling point 30° C./13 mbar; 2-(2′,2′-dimethoxyethyl)-4-methyl-(1,3)-dioxolane (64%) of boiling point 37° C./0.5 mbar;

malondialdehyde bis-1,2-propyleneacetal (17%) of boiling point 50° C./0.4 mbar; 1-methoxypropoxy-1,3,3-trimethoxypropane (5%) of boiling point 65°–70° C./0.4 mbar; and 2-(2-methoxy-2-methoxypropoxyethyl)-4-methyl-(1,3)-dioxolane (6%) of boiling point 65°–70° C./0.4 mbar.

EXAMPLE 2

1,000 parts of methylformate and 2 parts of $BF_3 \cdot HCOOCH_3$ are introduced into a reactor and heated to 30° C. A mixture of 110 parts of 1,2-propylene oxide and 50 parts of methylformate is then added over 2 hours at 30°–32° C., and the batch is concentrated until the boiling point reaches 70° C. 58 parts of methyl vinyl ether are then introduced over one hour at 20°–30° C. After addition of 2 parts of tetramethylethylenediamine to neutralize the catalyst, the reaction mixture is distilled as in Example 1. 46 parts of first runnings are obtained at 25°–50° C./25 mbar, whilst at 55°–85° C./1 mbar, 179 parts of crude end product I (87.4% pure) are obtained, corresponding to a yield of 46% of theory based on propylene oxide and 87.4% of theory based on methyl vinyl ether.

Composition of the pure end product: 4% of 1,1,3,3-tetramethoxypropane, boiling point 30° C./1.3 mbar; 76% of 2-(2',2'-dimethoxyethyl)-4-methyl-1,3-dioxolane, boiling point 37° C./0.5 mbar; 10% of malondialdehyde bis-1,2-propylene-acetal, boiling point 50° C./0.4 mbar; 5% of 1-methoxypropoxy-1,3,3-trimethoxypropane, boiling point 65° to 70° C./0.4 mbar; and 5% of 2-(2'-methoxy-2'-methoxypropoxyethyl)-4-methyl-1,3-dioxolane.

EXAMPLE 3

The procedure described in Example 2 is followed except that the first runnings from this experiment are mixed with 78 parts of methyl vinyl ether and this solution is added to the reaction mixture. Working up gives 51 parts of first runnings and 232 parts of crude end product I (88% pure) in a yield of 60% of theory, based on propylene oxide, and 88% of theory, based on methyl vinyl ether.

The composition of the end product corresonds to that in Example 2.

EXAMPLE 4

The following are passed continuously into a reactor: (a) 1,110 parts by volume/hour of methylformate, (b) 141 parts by volume/hour of a 50 percent strength by weight solution of propylene oxide in methyl formate and (c) 76 parts by volume/hour of an 0.8 percent by weight solution of $BF_3$ in methylformate. After a mean resistance time of 30 minutes at 33° C., the reaction mixture flows into a distillation apparatus in which excess methylformate is removed at 65° C. 1,110 parts by volume/hour of distillate, which is recycled to the first reaction vessel, and 217 parts by volume/hour of residue, which is pumped continuously into a second reactor, are obtained. At the same time, the second reactor is charged with 70 parts by volume/hour of a 50 percent strength by weight solution of methyl vinyl ether in methylformate. After a mean residence time of 30 minutes at 22°–26° C., the reaction mixture from the second reactor flows into a third reactor, where it is collected over a reaction time of 5 hours, and mixed with a total of 5 parts by volume of tetramethylethylenediamine.

Distillation of the reaction product as in Example 1 gives 630 parts of methylformate, 215 parts of first runnings and 346 parts of crude end product I (87% pure), in a yield of 33% based on propylene oxide or 63%, based on methyl vinyl ether.

The composition of the end product is as in Example 2.

EXAMPLE 5

The procedure described in Example 4 is followed, except for the following differences: the distillation is carried out at 73° C., giving 1,210 parts by volume/hour of distillate, which are recycled to the first reaction vessel, and the first runnings from Example 4 are used to dissolve the methyl vinyl ether. Working up the reaction mixture gives 544 parts of methylformate, 248 parts of first runnings and 560 parts of crude end product I (85.2% pure) in a yield of 50%, based on propylene oxide, or 70%, based on methyl vinyl ether.

The composition of the end product is as in Example 1.

EXAMPLE 6

The procedure described in Example 4 is followed, but instead of the propylene oxide solution 107 parts by volume/hour of a 50 percent strength by weight solution of ethylene oxide in methyl formate are used. In this example, only 40 parts by volume/hour of the methyl vinyl ether solution are employed. After working up as in Example 4, a mixture of 1,1,3,3-tetramethoxypropane, 2-(2',2'-dimethoxyethyl)-(1,3)-dioxolane, malondialdehyde bis-(ethyleneacetal), 1-methoxyethoxy-1,3,3-trimethoxypropane and 2-(2'-methoxy-2'-methoxyethoxy-ethyl)-(1,3)-dioxolane is obtained as the end product, the composition being as in Example 2.

We claim:

1. A process for the preparation of malondialdehyde tetraalkylacetals of the formula $$\begin{array}{c} R^1-O \\ \phantom{R^1-}\diagdown \\ \phantom{R^1-O}CH-CH_2-CH \\ \phantom{R^1-}\diagup \phantom{CH-CH_2-}\diagdown \\ R^1-O \phantom{CH-CH_2-CH}O-R^1 \\ \phantom{CH-CH_2-CH}O-R^1 \end{array} \qquad \text{I}$$

where the individual radicals $R^1$ may be identical or different and each is alkyl, or alkoxy-substituted alkyl, and 2 adjacent $R^1$'s may also be $$-CH_2-\underset{\underset{R^2}{|}}{CH}-,$$

where $R^2$ is hydrogen or alkyl, which process comprises:

reacting an alkyl formate of the formula $$HCOOR^1 \qquad \text{II}$$

with an oxirane of the formula $$\underset{H_2C}{\overset{O}{\diagup\phantom{x}\diagdown}}CH-R^2 \qquad \text{III}$$

and an alkyl vinyl ether of the formula $$CH_2=CH-OR^1 \qquad \text{IV}$$

where $R^1$ and $R^2$ have the above meanings, in the presence of a catalyst selected from the group consisting of the halides of boron, antimony(V), iron(III), tin(II or IV) and zinc, using from 0.5 to 3.0 moles of starting material II per mole of starting material IV.

2. A 2(2',2'-dialkoxyethyl)-4-alkyl-(1,3)-dioxolane of the formula

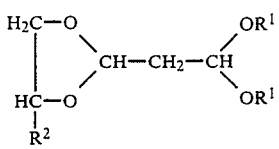
Ia where the individual radicals $R^1$ may be identical or different and each is alkyl or alkoxy-substituted alkyl, and the pair of $R^1$ radicals may also be

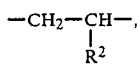

if $R^2$ is hydrogen or alkyl of more than one carbon atom,

3. A process as claimed in claim 1, wherein from 0.5 to 3.0 moles of starting material II are usd per mole of starting material IV.

4. A process as claimed in claim 1, wherein from 0.05 to 5.0% by weight of halide, based on the amount by weight of starting material II, are employed.

5. A process as claimed in claim 1, wherein the reaction temperature is from $-80°$ to $+200°$ C.

6. A process as claimed in claim 1, wherein the reaction temperature is from $0°$ to $100°$ C.

7. A process as claimed in claim 1, wherein the reaction pressure is from 1 to 4 bar.

8. A process as claimed in claim 1, wherein a solvent is employed.

9. A process as claimed in claim 1, using
(a) from 0.5 to 3.0 moles of starting material II per mole of starting material IV and
(b) from 0.05 to 5.0% by weight of the halide catalyst, based on the amount by weight of starting material II, and carrying out the reaction at a temperature of from $-80°$ to $+200°$ C. and a pressure of from 1 to 4 bar.

10. A process as claimed in claim 9 using a reaction temperature of from $0°$ to $100°$ C.

11. A process as claimed in claim 9 using a reaction temperature of from $20°$ to $70°$ C.

12. A process as claimed in claim 1 using starting material II as a solvent as well as a reactant in a total amount of 5 to 40 moles per mole of starting material IV.

13. A process as claimed in claim 9 using a solvent selected from the group consisting of aromatic and aliphatic hydrocarbons, halohydrocarbons, carboxylic acid esters and ethers.

14. A dioxolane as claimed in claim 2 wherein $R^1$ is alkyl of 1 to 6 carbon atoms which is unsubstituted or substituted by alkoxy of 1 to 4 carbon atoms, or wherein two adjacent $R^1$'s may be

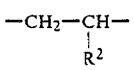

wherein $R^2$ is hydrogen or alkyl of 1 to 6 carbon atoms.

15. A dioxolane as claimed in claim 2 which is 2-(2',2'-dimethoxyethyl)-4-methyl-(1,3)-dioxolane.

16. A dioxolane as claimed in claim 2 which is 2-(2',2'-dimethoxyethyl)-(1,3)-dioxolane.

17. A dioxolane as claimed in claim 2 which is 2-(2'-methoxy-2'-methoxyethoxy-ethyl)-(1,3)-dioxolane.

* * * * *